United States Patent [19]

Cereda et al.

[11] Patent Number: 4,699,915
[45] Date of Patent: Oct. 13, 1987

[54] SUBSTITUTED HETEROCYCLYL-PHENYLFORMAMIDINES AND SALTS THEREOF

[75] Inventors: Enzo Cereda, Tortona; Giuseppe Bietti; Arturo Donetti, both of Milan; Piero del Soldato, Monza; Antonio Giachetti, Milan; Ferdinando Pagani, Verano Brianza, all of Italy

[73] Assignee: Istituto de Angeli S.p.A., Milan, Italy

[21] Appl. No.: 751,087

[22] Filed: Jul. 2, 1985

Related U.S. Application Data

[63] Continuation-in-part of Ser. No. 491,367, May 4, 1983, abandoned.

[30] Foreign Application Priority Data

May 18, 1982 [IT] Italy ............... 21331 A/82

[51] Int. Cl.$^4$ ............... A61K 31/41; A61K 31/415; C07D 231/12; C07D 249/08
[52] U.S. Cl. ............... 514/357; 514/365; 514/383; 514/406; 546/330; 546/332; 548/202; 548/203; 548/205; 548/269; 548/373
[58] Field of Search ............... 548/202, 203, 205, 269, 548/273; 546/330, 332; 514/357, 365, 383, 406

[56] References Cited

U.S. PATENT DOCUMENTS 4,386,099 5/1983 Cereda et al. ............... 548/346 X
4,438,127 3/1984 Durant et al. ............... 548/336 X

FOREIGN PATENT DOCUMENTS 1296544 11/1972 United Kingdom .

Primary Examiner—Richard L. Raymond
Attorney, Agent, or Firm—Hammond & Littell, Weissenberger & Dippert

[57] ABSTRACT

Compounds of the formula

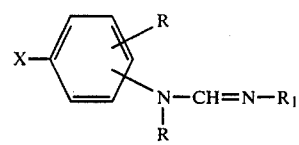

wherein
R is hydrogen or methyl;
$R_1$ is straight or branched alkyl of 1 to 6 carbon atoms, hydroxy(alkyl of 1 to 6 carbon atoms), mono- or di-(alkoxy of 1 to 6 carbon atoms)(alkyl of 1 to 6 carbon atoms), (alkyl of 1 to 6 cabon atoms)thio(alkyl of 1 to 6 carbon atoms), cyano(alkyl of 1 to 6 carbon atoms), alkenyl, alkynyl, or cycloalkyl;
$R_2$ is hydrogen, alkyl of 1 to 3 carbon atoms, alkoxy of 1 to 3 carbon atoms or halogen; and
X is pyrazol-3-yl, 1,2,4-triazol-3-yl, pyridin-2-yl, pyridin-3-yl, thiazol-4-yl, 2-methyl-thiazol-4-yl or 2-methylamino-thiazol-4-yl;

tautomers thereof, and non-toxic, pharmacologiically acceptable acid addition salts thereof. The compounds as well as their salts are useful as antiulcerogenics and gastric acid secretion inhibitors.

9 Claims, No Drawings

SUBSTITUTED HETEROCYCLYL-PHENYLFORMAMIDINES AND SALTS THEREOF

This is a continuation-in-part of copending application Ser. No. 491,367, filed May 4, 1983, now abandoned.

This invention relates to novel substituted heterocyclylphenylformamidines and acid addition salts thereof, to methods of preparing these compounds, to pharmaceutical compositions containing them as active ingredients, and to methods of using them as gastric acid secretion inhibitors and antiulcerogenics.

BACKGROUND OF THE INVENTION AND THE PRIOR ART

It is known that classic antihistamines, such as mepyramine, are capable of antagonizing some effects of histamine mediated by $H_1$-receptors. However, these compounds have no effect on gastric acid secretion which is instead affected by other antihistaminic agents defined by Black et al. (Nature 236, 385, 1972) as histamine $H_2$-receptor antagonists. This has indicated that another kind of receptors ($H_2$) already described by Ash and Schild (Brit. J. Pharmacol. Chem. Ther. 1966, 27, 427–39), is involved in the gastric secretory response which is not blocked by the conventional antihistamines of the $H_1$-type.

Examples of $H_2$-receptor antagonists capable of antagonizing gastric acid secretion include burimamide, metiamide, and cimetidine. More recently, new $H_2$-antagonists, such as rantidine (Bradshaw et al., Brit. J. Pharmacol. 66, 464P, 1979), tiotidine (P. O. Jellin, Life Sci. 25, 2001, 1979) and BL 6341 (Cavanagh et al., Fed. Proc., 40, 2652, 1981) have been discovered. These compounds are effective $H_2$-blockers capable of antagonizing gastric acid secretion to a greater extent than cimetidine and congeners. In copending U.S. application Ser. No. 465,572, filed Feb. 10, 1983, now U.S. Pat. No. 4,548,944, and U.S. Pat. No. 4,386,099 we have described new classes of histamine $H_2$-antagonists, namely imidazolyl-phenylamidines and guanidino-heterocyclylphenylamidines, which are potent $H_2$-blockers and active antagonists of gastric acid secretion. These compounds do not resemble the so far known $H_2$-antagonists, such as cimetidine, ranitidine, etc., and are characterized by a phenylformamidine grouping bearing variously substituted imidazolyl- and guanidino-heterocyclyl rings.

DESCRIPTION OF THE INVENTION

More particularly, the present invention relates to a novel class of heterocyclyl-phenylformamidines represented by the formula

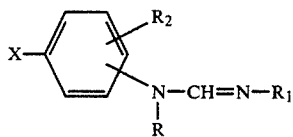

(I)

wherein
R is hydrogen or methyl;
$R_1$ is straight or branched alkyl of 1 to 6 carbon atoms, hydroxy(alkyl of 1 to 6 carbon atoms), mono- or di-(alkoxy of 1 to 6 carbon atoms) (alkyl of 1 to 6 carbon atoms), (alkyl of 1 to 6 carbon atoms)thio(alkyl of 1 to 6 carbon atoms), cyano(alkyl of 1 to 6 carbon atoms), alkenyl, alkynyl or cycloalkyl;
$R_2$ is hydrogen, alkyl of 1 to 3 carbon atoms, alkoxy of 1 to 3 carbon atoms or halogen; and
X is pyrazol-3-yl, 1,2,4-triazol-3-yl, pyridin-2-yl, pyridin-3-yl, thiazol-4-yl, 2-methyl-thiazol-4-yl or 2-methylamino-thiazol-4-yl;
tautomers thereof, and non-toxic, pharmacologically acceptable acid addition salts thereof.

It is to be understood that, although the double bond in the formamidine radical has been inserted in a particular position, other tautomeric forms are possible when R is hydrogen, and that in the substituted X different tautomeric forms are also possible. The present invention includes such tautomeric forms within its scope, both in terms of the compounds of the invention and in terms of the methods of preparation.

More particularly, when $R_1$ is hydroxy(alkyl of 1 to 6 carbon atoms) it may be hydroxypropyl or hydroxybutyl; when $R_1$ is mono- or di-(alkoxy of 1 to 6 carbon atoms) it may be hydroxypropyl or hydroxybutyl; when $R_1$ is mono- or di-(alkoxy of 1 to 6 carbon atoms) (alkyl of 1 to 6 carbon atoms) it may be mono- or dimethoxyethyl or methoxypropyl; when $R_1$ is (alkyl of 1 to 6 carbon atoms)thio(alkyl of 1 to 6 carbon atoms) it may be methylthioethyl or ethylthioethyl; when $R_1$ is cyano-(alkyl of 1 to 6 carbon atoms) it may be cyanoethyl; when $R_1$ is alkenyl it may be alkenyl of 3 to 5 carbon atoms; when $R_1$ is alkynyl it may be alkynyl of 3 to 4 carbon atoms; when $R_1$ is cycloalkyl it may be cycloalkyl of 3 to 6 carbon atoms; and when $R_2$ is halogen it may be bromine, chlorine, or fluorine.

In formula I the formamidine radical may be in the ortho-, meta- or para-position of the benzene ring with respect to X, and substituent $R_2$ may be in any position on the benzene ring.

Preferred compounds according to the present invention include those wherein the formamidine radical is in the para-position on the phenyl ring with respect to substituent X; R represents a hydrogen atom; $R_1$ is propyl, isopropyl, butyl, sec.butyl, isobutyl, neopentyl, allyl, methoxyethyl, dimethoxyethyl, hydroxypropyl, hydroxybutyl, methylthioethyl, ethylthioethyl or cyanoethyl; $R_2$ is hydrogen, methyl, methoxy, bromine, chlorine or fluorine; and X is pyrazol-3-yl or 1,2,4-triazol-3-yl; and their non-toxic, pharmacologically acceptable acid addition salts.

Such compounds generally have better activity and are therefore preferred as antisecretory-antiulcer agents and for the treatment of disorders of the gastrointestinal tract.

The compounds of the formula I may, for example, be prepared by the following method:

Reaction of an N,N'-disubstituted formamidine of the formula:

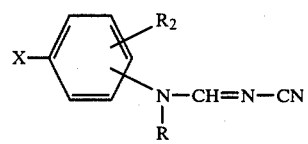

(II)

wherein X, R and $R_2$ have the meanings previously defined, with an amine of the formula $$H_2N-R_1 \quad (III)$$

wherein $R_1$ has the meanings previously defined.

The reaction may conveniently be performed in the presence of water or of an inert aqueous organic solvent, for example in a lower alkanol such as methanol or ethanol, formamide, dimethylformamide, dioxane or acetonitrile. The reaction is generally carried out at a temperature from 10° to 50° C., preferably at room temperature.

The compounds of the formula II used as starting material in this method may be prepared by methods which are described in the literature, for example, by reacting an amine of the formula

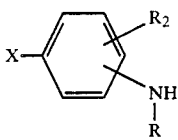

wherein X, R and $R_2$ have the meanings previously defined, with an N-cyano-alkylimidate of the formula

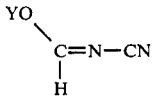

in which Y is lower alkyl, such as methyl or ethyl. The reaction may generally be carried out in the presence of a suitable inert organic solvent, such as a lower alkanol, an ether, ethylacetate, acetonitrile or dioxane, or also without solvent, at a temperature from 20° to 80° C., preferably at room temperature.

Optionally, the compounds of the formula II may be prepared in a single step by reacting an amine of the formula IV with cyanamide in the presence of a compound of the formula

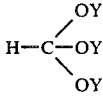

in which Y has the meaning previously defined. The reaction is carried out at a temperature of 50° to 150° C.

The compounds of the formula I prepared according to the above method may optionally be converted with inorganic or organic acids into non-toxic, pharmacologically acceptable acid addition salts, for example by conventional methods such as by reacting the compounds as bases with a solution of the corresponding acid in a suitable solvent, or by adding the acid solution directly to the reaction mixture obtained in the method without isolation of the compound as a base.

Particularly preferred acids include for example hydrochloric, sulfuric, maleic and fumaric acid. The compounds of the formula I and their non-toxic, pharmacologically acceptable acid addition salts are $H_2$-receptor blocking agents which inhibit gastric acid secretion.

Particularly preferred compounds of the present invention are the following:

N-Isopropyl-N'-[4-(pyrazol-3-yl)-phenyl]-formamidine, and

N-Isopropyl-N'-[4-(1,2,4-triazol-3-yl)-phenyl]-formamidine.

The following examples illustrate the present invention and will enable others skilled in the art to understand it more completely. It should be understood, however, that the invention is not limited solely to the particular examples given below.

PREPARATION OF STARTING COMPOUNDS

Example 1

3-(4-Aminophenyl)-pyrazole (a) A mixture of 4-nitroacetophenone (24.8 g) and N,N'-dimethyl formamide diethyl acetal (33.1 g) was refluxed for 17 hours. 27.4 g of 1-(4-nitrophenyl)-3-N,N-dimethylamino-2-propen-1-one were obtained by crystallizing the residue from diethyl ether; M.p. 148° C.

(b) A solution of 1-(4-nitrophenyl)-3-N,N-dimethylamino-2-propen-1-one (27.3 g) and 85% hydrazine hydrate (23.6 g) in ethanol was heated at 60° C. for one hour. The crystallized solid was filtered to give 18.5 g of 3-(4-nitrophenyl)-pyrazole; M.p. 196°–197° C.

(c) To a refluxing suspension of 3-(4-nitrophenyl)-pyrazole (18 g) and Raney nickel (3.3 g) in methanol (190 ml) was added dropwise a solution of 85% hydrazine hydrate (22 g) in methanol (50 ml). The solution was refluxed for 30 minutes more, filtered and evaporated to dryness. The oily residue, after crystallization from water, furnished 14.5 g of 3-(4-aminophenyl)-pyrazole; M.p. 104° C. 3-(3-Aminophenyl)-pyrazole, M.p. 144°–145° C., was prepared in a similar manner starting from 3-nitroacetophenone.

Example 2

3-(3-Methyl-4-amino-phenyl)-1,2,4-triazole (a) A mixture of 2-methyl-4-nitro-benzamide (15 g) and N,N-dimethylformamide diethyl acetale (29 ml) was heated to 120° C. to remove the ethanol formed. After 90 minutes the solid residue was treated with petroleum ether and filtered to give 18.9 g of N,N-Dimethyl-N'-(2-methyl-4-nitrobenzoyl)-formamidine; M.p. 118°–121° C.

(b) N-N-Dimethyl-N'-(2-methyl-4-nitro-benzoyl)-formamidine (18.8 g) was added portionwise to a stirred solution of hydrazine monohydrate 99% (4.8 g) in glacial acetic acid (196 ml). The suspension was heated at 90° C. for 90 minutes. The solution was concentrated to a small volume in a vacuum, and the residue was diluted with diethyl ether (100 ml). The solid which separated out was filtered off and dried to give 15.8 g of 3-(3-Methyl-4-nitro-phenyl)-1,2-4-triazole; M.p. 204°–206° C.

(c) A solution of $Na_2S.8H_2O$ (171.89 g) in methanol (690 ml) and water (173 ml) was added dropwise to a refluxing suspension of 3-(3-methyl-4-nitro-phenyl)-1,2,4-triazole (36.8 g) in methanol (170 ml). After two hours of refluxing, the solution was filtered through charcoal and evaporated to dryness. The residue was dissolved in 10% hydrochloric acid, the solution was washed several times with ethyl acetate and neutralized with $NaHCO_3$ solution. The solid which separated out was filtered off and dried to give 25.9 g of the title compound; M.p. 183°–186° C. 3-(3-Methoxy-4-aminophenyl)-1,2,4-triazole; M.p. 191°–194° C., was prepared in analogous manner.

Example 3

N-Methyl-N-[4-(pyrazol-3-yl)-phenyl]-amine (a) A solution of 3-(4-aminophenyl)-1-H-pyrazole (10 g) in formic acid (100 ml) was refluxed for 4 hours and evaporated to dryness. The residue was dissolved in water, and the solution was filtered through charcoal. The filtrate was made basic to give 9.5 g of N-[4-(pyrazol-3-yl)-phenyl]-formamide; M.p. 139°–141° C.

(b) A suspension of N-[4-pyrazol-3-yl)-phenyl]-formamide (7.5 g) in anhydrous tetrahydrofuran (80 ml) was slowly added dropwise to a suspension of LiAlH$_4$ (6 g) in anhydrous tetrahydrofuran. The reaction mixture was refluxed for 4 hours and cooled. Wet diethyl ether was added and the solution was evaporated to dryness. The residue was dissolved in a mixture of water and ethylacetate. After working up the organic layer, 4.1 g of N-Methyl-N-[4-(pyrazol-3-yl)-phenyl]-amine; M.p. 78°–86° C. were obtained.

Example 4

2-Methylamino-4-(3-amino-phenyl)-thiazole (a) A mixture of ethyl N-[3-(2-brmoacetyl)-phenyl]-carbamate (28.6 g), 1-methyl-thiourea (9 g) and ethanol (75 ml) was refluxed for 4 hours and then cooled. The precipitate was filtered off and washed with cold ethanol to give 34.5 g of ethyl N-[3-(2-methylamino-4-thiazolyl)-phenyl]-carbamate hydrobromide; M.p. 140°–141° C.

(b) A mixture of ethyl N-[3-(2-methylamino-4-thiazolyl)-phenyl]-carbamate hydrobromide (33.5 g) and 10% hydrochloric acid (500 ml) was refluxed for 48 hours. After cooling, the solution was made alkaline with 10% sodium hydroxide and the precipitate was filtered off, washed with water and dried to give 16.5 g of 2-methylamino-4-(3-amino-phenyl)-thiazole; M.p. 118°–121° C. 2-Methylamino-4-(4-amino-phenyl)-thiazole; M.p. 178°–180° C., was prepared in analogous manner, starting from the appropriate carbamate derivative.

Example 5

2-Methyl-4-(3-amino-phenyl)-thiazole

A mixture of 3-amino-phenacyl bromide hydrobromide (11.78 g), thioacetamide (3 g) and dimethylformamide (20 ml) was stirred at room temperature for 24 hours and then poured into water (100 ml). The resulting solution was made alkaline with 10% sodium hydroxide, and the precipitate was filtered off and dried to give 6 g of 2-methyl-4-(3-amino-phenyl)-thiazole; M.p. 134°–137° C.

Example 6

3-[(3-chloro-4-amino)-phenyl]-1-H-pyrazole (a) A solution of N-[2-chloro-4-acetyl-phenyl]-acetamide (4.6 g) in N,N'-dimethyl-formamide diethyl acetal (8.5 g) was refluxed for 18 hours. The reaction mixture was cooled, and the precipitate was crystallized from diethyl ether, filtered off and added to a solution of 85% hydrazine hydrate (11.5 g) in ethanol. The reaction mixture was heated at 60° C. for one hour. The crystallized solid was filtered off to give 3.5 g of 3-[(3-chloro-4-acetamido)-phenyl]-1-H-pyrazole; M.p. 185°–188° C.

(b) A solution of this compound (2 g) in 6N hydrochloric acid (7 ml) was heated at 80° C. for 20 minutes and then neutralized with 10% NaOH. The oily product which separated out was extracted with ethyl acetate, and the extract was washed and evaporated to dryness to give 1.1 g of 3-[(3-chloro-4-amino)-phenyl]-1-H-pyrazole as a thick reddish oil.

In analogous manner, starting from the appropriate intermediates, the following pyrazole derivatives were prepared 3-[3-bromo-4-amino)-phenyl]-1-H-pyrazole, yellow oil. 3-[(3-fluoro-4-amino)-phenyl]-1-H-pyrazole; M.p. 60°–62° C.

Example 7

N-Cyano-N'-[4-(pyrazol-3-yl)-phenyl]-formamidine

A solution of 3-(4-aminophenyl)-pyrazole (15.9 g) and N-cyano ethyl formimidate (9.8 g) in acetone (100 ml) was stirred overnight at room temperature. The solid which crystallized out was filtered off and dried to give 12.5 g of the title compound; M.p. 223°–224° C.

By utilizing the above procedure the following compound was also prepared:

N-Cyano-N'-[3-(pyrazol-3-yl)-phenyl]-formamidine; M.p. 194°–197° C.

Example 8

N-Cyano-N'-[4-(pyridin-2-yl)-phenyl]-formamidine

A mixture of 2-(4-amino-phenyl)-pyridine (3.1 g), cyanamide (0.8 g) and triethyl orthoformate (3.6 g) was heated at 150° C. for a few minutes. The product which crystallized out was filtered off, washed with ethanol and dried to give 2.5 g of the title compound; M.p. 150°–151° C.

The following compounds were prepared in analogous manner:

N-Cyano-N'-[4-(pyridin-3-yl)-phenyl]-formamidine; M.p. 227°–228° C.

N-Cyano-N'-[(2-methyl-4-(1,2,4-triazol-3-yl)-phenyl]-formamidine; M.p. 285°–287° C. (dec.).

N-Cyano-N'-[(2-methoxy-4-(1,2,4-triazol-3-yl)-phenyl]-formamidine; M.p. 268°–270° C. (dec.).

Example 9

N-Cyano-N'-[3-(1,2,4-triazol-3-yl)-phenyl]-formamidine

A solution of 3-(4-amino-phenyl)-1,2,4-triazole (9.85 g) and N-cyano ethyl formimidate (5.1 g) in ethanol (100 ml) was stirred overnight at room temperature. The solid which crystallized out was filtered off and dried to give 12.5 g of the title compound; M.p. 247°–250° C. (dec.).

The following compounds were prepared in analogous manner:

N-Cyano-N'-[(2-fluoro-4-(pyrazol-3-yl)-phenyl]-formamidine; M.p. 220°–223° C. (dec.), N-Cyano-N'-[(2-chloro-4-(pyrazol-3-yl)-phenyl]-formamidine; M.p. 231°–232° C. (dec.), N-Cyano-N'-[3-(2-amino-thiazol-4-yl)-phenyl]-formamidine; M.p. 152°–155° C., N-Cyano-N'-[3-(2-methylamino-thiazol-4-yl)-phenyl]-formamidine; M.p. 181°–183° C., N-Cyano-N'-[4-(2-methylamino-thiazol-4-yl)-phenyl]-formamidine; M.p. 192°–196° C. (dec.), N-Cyano-N'-[3-(2-methyl-thiazol-4-yl)-phenyl]-formamidine; M.p. 202°–205° C., N-Cyano-N'-[4-(2-methyl-thiazol-4-yl)-phenyl]-formamidine; M.p. 210°–212° C., and N-Cyano-N'-[4-(thiazol-4-yl)-phenyl]-formamidine; M.p. 218°–220° C. (dec.).

PREPARATION OF END PRODUCTS OF THE FORMULA I

Example 10

N-Isopropyl-N'-[4-(1,2,4-triazol-3-yl)-phenyl]-formamidine

A solution of N-Cyano-N'-[4-(1,2,4-triazol-3-yl)-phenyl]-formamidine (3 g) and isopropylamine (8.5 g) in water (1.5 ml) was stirred for twenty minutes. The crystallized solid was filtered off and purified via its maleate salt in ethanol.

Yield: 2.7 g; M.p. 156°–157° C. (dec.).
Analysis: $C_{20}H_{23}N_5O_8$: Found %: C-52.38; H-5.21; N-14.98. Calc. %: C-52.06; H-5.02; N-15.18.

Substitution of the appropriate N-cyano-formamidine derivative and amino compound for those of Example 10 and utilizing the procedure there described led to the production of the following formamidines:

(a) N-Isopropyl-N'-[4-(pyrazol-3-yl)-phenyl]-formamidine

Hydrochloride (acetone); M.p. 202°–203° C. (dec.).
Analysis: $C_{13}H_{18}Cl_2N_4$: Found %: C-51.57; H-5.98; N-18.28. Calc. %: C-51.83; H-6.02; N-18.60.

(b) N-Allyl-N'-[4-(pyrazol-3-yl)-phenyl]-formamidine

Hydrochloride (acetone); M.p. 212°–213° C. (dec.).
Analysis: $C_{13}H_{16}Cl_2N_4$: Found %: C-52.42; H-5.48; N-18.78. Calc.%: C-52.18; H-5.39; N-18.73.

(c) N-sec.Butyl-N'-[4-(pyrazol-3-yl)-phenyl]-formamidine

Hydrochloride (acetone); M.p. 209°–210° C. (dec.).
Analysis: $C_{14}H_{20}Cl_2N_4$: Found %: C-53.23; H-6.60; N-17.66. Calc. %: C-53.34; H-6.39; N-17.77.

(d) N-Propyl-N'-[4-(pyrazol-3-yl)-phenyl]-formamidine

Hydrochloride (ethanol); M.p. 199°–201° C. (dec.).
Analysis: $C_{13}H_{18}Cl_2N_4$: Found %: C-51.23; H-6.09; N-18.54. Calc. %: C-51.18; H-6.02; N-18.60.

(e) N-(2-Methylthio-ethyl)-N'-[4-(pyrazol-3-yl)-phenyl]formamidine

Nitrate (ethanol); M.p. 141° C. (dec.).
Analysis: $C_{13}H_{17}N_5O_3S$: Found %: C-48.11; H-5.32; N-21.73. Calc.%: C-48.28; H-5.29; N-21.66.

(f) N-n-Propyl-N'-[4-(1,2,4-triazol-3-yl)-phenyl]-formamidine

Maleate (acetone); M.p. 140°–142° C. (dec.).
Analysis: $C_{20}H_{23}N_5O_8$: Found %: C-51.83; H-5.15; N-15.00. Calc. %: C-52.06; H-5.02; N-15.18.

(g) N-sec.-Butyl-N'-[4-(1,2,4-triazol-3-yl)-phenyl]-formamidine

Maleate (acetone); M.p. 152°–154° C. (dec.).
Analysis: $C_{21}H_{25}N_5O_8$: Found %: C-52.77; H-5.32; N-14.64. Calc. %: C-53.05; H-5.30; N-14.73.

(h) N-Allyl-N'-[4-(1,2,4-triazol-3-yl)-phenyl]-formamidine

Maleate (acetone); M.p. 146°–148° C. (dec.).
Analysis: $C_{16}H_{17}N_5O_4$: Found %: C-55.64; H-5.04; N-20.46. Calc. %: C-55.97; H-4.99; N-20.40.

(i) N-(2-Methoxy-ethyl)-N'-[4-(1,2,4-triazol-3-yl)-phenyl]-formamidine

Fumarate (acetone); M.p. 182°–184° C. (dec.).
Analysis: $C_{16}H_{19}N_5O_5$: Found %: C-53.01; H-5.35; N-19.53. Calc. %: C-53.18; H-5.30; N-19.38.

(j) N-Isopropyl-N'-[3-(2-methyl-thiazol-4-yl)-phenyl]-formamidine

M.p. 110°–112° C. (dec).
Analysis: $C_{14}H_{17}N_3S$: Found %: C-63.56; H-6.85; N-16.30. Calc. %: C-63.83; H-6.61; N-16.20.

(k) N-Ethyl-N'-[4-(2-methyl-thiazol-4-yl)-phenyl]-formamidine

M.p. 119°–120° C. (dec.).
Analysis: $C_{13}H_{15}N_3S$: Found %: C-63.41; H-6.18; N-17.01. Calc. %: C-63.64; H-6.16; N-17.13.

(l) N-n-Propyl-N'-[4-(2-methyl-thiazol-4-yl)-phenyl]-formamidine

M.p. 112°–115° C. (dec.).
Analysis: $C_{14}H_{17}N_3S$: Found %: C-64.04; N-6.72; N-15.96. Calc. %: C-63.83; H-6.61; N-16.20.

(m) N-Isopropyl-N'-[4-(2-methyl-thiazol-4-yl)-phenyl]-formamidine

M.p. 119°–120° C. (dec.).
Analysis: $C_{14}H_{17}N_3S$: Found %: C-63.52; H-6.42; N-16.20. Calc.%: C-63.83; H-6.61; N-16.20.

(n) N-Isopropyl-N'-[4-(thiazol-4-yl)-phenyl]-formamidine

M.p. 110°–113° C. (dec.).
Analysis: $C_{13}H_{15}N_3S$: Found %: C-60.24; H-5.91; N-17.34. Calc. %: C-63.36; H-6.16; N-17.13.

(o) N-Propargyl-N'-[4-(thiazol-4-yl)-phenyl]-formamidine

M.p. 129°–132° C. (dec.).
Analysis: $C_{13}H_{11}N_3S$: Found %: C-64.40; H-4.49; N-17.42. Calc. %: C-64.72; H-4.60; N-17.42.

(p) N-Ethyl-N'-[3-(pyrazol-3-yl)-phenyl]-formamidine

Hydrobromide (acetone); M.p. 80°–81° C. (dec.).
Analysis: $C_{12}H_{15}BrN_4$: Found %: C-48.95; H-5.23; N-18.57. Calc. %: C-48.82; H-5.12; N-18.98.

(q) N-n-Propyl-N'-[3-(pyrazol-3-yl)-phenyl]-formamidine

Hydrochoride (acetone); M.p. 160°–162° C. (dec.).
Analysis: $C_{13}H_{17}ClN_4$: Found %: C-58.48; H-6.34; N-20.98. Calc. %: C-58.97; H-6.47; N-21.16.

(r) N-sec.Butyl-N'-[4-(pyridin-3-yl)-phenyl]-formamidine

Maleate (ethyl acetate); M.p. 130°–135° C. (dec.).
Analysis: $C_{24}H_{27}N_3O_8$: Found %: C-59.08; H-5.53; N-8.57. Calc. %: C-59.37; H-5.60; N-8.66.

(s) N-Isopropyl-N'-[4-(pyridin-3-yl)-phenyl]-formamidine

Maleate (ethyl acetate); M.p. 129°–130° C. (dec.).

Analysis: $C_{23}H_{25}N_3O_8$: Found %: C-58.80; H-5.09; N-8.69. Calc. %: C-58.58; H-5.35; N-8.91.

(t)

N-Isopropyl-N'-[4-(pyridin-2-yl)-phenyl]-formamidine

Maleate (ethyl acetate); M.p. 172°–173° C. (dec.).
Analysis: $C_{23}H_{26}N_3O_8$: Found %: C-58.38; H-5.38; N-8.65. Calc. %: C-58.58; H-5.35; N-8.91.

(u)

N-n-Hexyl-N'-[4-(pyridin-2-yl)-phenyl]-formamidine

Maleate (ethyl acetate); M.p. 138°–140° C. (dec.).
Analysis: $C_{22}H_{27}N_3O_4$: Found %: C-66.82; H-6.87; N-10.53. Calc. %: C-66.48; H-6.85; N-10.57.

(v) N-Allyl-N'-[4-(pyridin-2-yl)-phenyl]-formamidine

Maleate (ethyl acetate); M.p. 120° C. (dec.).
Analysis: $C_{19}H_{19}N_3O_4$: Found %: C-64.73; H-5.78; N-11.29. Calc. %: C-64.58; H-5.42; N-11.89.

(w)

N-sec.Butyl-N'-[4-(pyridin-2-yl)-phenyl]-formamidine

Maleate (ethyl acetate): M.p. 126°–127° C. (dec.).
Analysis: $C_{24}H_{27}N_3O_8$: Found %: C-59.71; H-5.44; N-8.75. Calc. %: C-59.37; H-5.61; N-8.65.

(x)

N-Cyclopropyl-N'-[4-(pyridin-2-yl)-phenyl]-formamidine

Maleate (ethyl acetate); M.p. 130°–134° C. (dec.).
Analysis: $C_{23}H_{23}N_3O_8$: Found % :C-58.80; H-4.98; N-9.09. Calc.: C-58.84; H-5.94; N-8.95.

(y)

N-Isopropyl-N'-[3-(pyridin-2-yl)-phenyl]-formamidine

Tartrate (ethyl acetate); M.p. 170° C. (dec.).
Analysis: $C_{19}H_{23}N_3O_6$: Found %: C-58.92; H-6.02; N-10.64. Calc. %: C-58.60; H-5.95; N-10.79.

(z) N-Allyl-N'-[3-(pyridin-2-yl)-phenyl]-formamidine

Tartrate (ethyl acetate); M.p. 150°–154° C. (dec.).
Analysis: $C_{34}H_{36}N_6O_6$: Found %: C-65.15; H-5.77; N-13.23. Calc. %: C-65.36; H-5.80; N-13.45.

(aa)

N-Methyl-N'-[3-(2-amino-thiazol-4-yl)-phenyl]-formamidine

Maleate (ethanol): M.p. 168°–169° C. (dec.).
Analysis: $C_{19}H_{20}N_4O_8S$: Found %: C-49.18; H-4.25; N-11.74. Calc. %: C-49.14; H-4.34; N-12.06.

(ab)

N-Isopropyl-N∝-[3-(2-amino-thiazol-4-yl)-phenyl]-formamidine

Maleate (ethanol); M.p. 162°–163° C. (dec.).
Analysis: $C_{21}H_{24}N_4O_8S$: Found %: C-50.95; H-4.85; N-11.32. Calc. %: C-51.21; H-4.91; N-11.37.

(ac)

N-Isopropyl-N'-[3-(2-methylamino-thiazol-4-yl)-phenyl]-formamidine

Maleate (ethanol); M.p. 152°–153° C.
Analysis: $C_{22}H_{26}N_4O_8S$: Found %: C-52.45; H-5.24; N-10.97. Calc. %: C-52.17; H-5.18; N-11.06.

(ad)

N-Isopropyl-N'-[4-(2-methylamino-thiazol-4-yl)-phenyl]-formamidine

Maleate (ethanol); M.p. 162°–163° C. (dec.).
Analysis: $C_{22}H_{26}N_4O_8S$: Found %: C-52.39; H-5.17; N-11.20. Calc. %: C-52.17; H-5.18; N-11.06.

(ae)

N-Neopentyl-N'-[4-(1,2,4-triazol-3-yl)-phenyl]-formamidine

Maleate (acetone); M.p. 144°–146° C. (dec.).
Analysis: $C_{22}H_{27}N_5O_8$: Found %: C-54.17; H-5.62; N-14.41. Calc. %: C-53.98; H-5.56; N-14.31.

(af)

N-Propargyl-N'-[4-(Pyrazol-3-yl)-phenyl]-formamidine

Hydrochloride (acetone); M.p. 199°–202° C. (dec.).
Analysis: $C_{12}H_{12}Cl_2N_4$: Found %: C-51.06; H-4.31; N-19.69. Calc. %: C-50.09; H-4.27; N-19.78.

(ag) N-(2-Cyano ethyl)-N'-[4-(pyrazol-3-yl)-phenyl]-formamidine

Hydrochloride (acetone); M.p. 208°–209° C. (dec.).
Analysis: $C_{13}H_{15}Cl_2N_5$: Found %: C-50.40; H-4.71; N-22.45. Calc. %: C-50.01; H-4.84; N-22.43

(ah) N-(2-Hydroxy ethyl)-N'-[2-fluoro-4-(pyrazol-3-yl)-phenyl]-formamidine

Hydrochloride (ethylacetate); M.p. 153°–157° C. (dec.).
Analysis: $C_{12}H_{15}FCl_2N_4$: Found %: C-47.02; H-4.88; N-18.25. Calc. %: C-47.23; H-4.95; N-18.36.

(ai)

N-Isopropyl-N'-[2-chloro-4-(pyrazol-3-yl)-phenyl]formamidine

Hydrochloride (ethanol); M.p. 184°–185° C. (dec.).
Analysis: $C_{13}H_{17}Cl_3N_4$: Found %: C-40.80; H-5.02; N-16.74. Calc. %: C-46.52; H-5.1; N-16.69.

(aj)

N-(2-Methylthioethyl)-N'-[2-methoxy-4-(1,2,4-triazol-3-yl)-phenyl]-formamidine

Maleate (ethanol); M.p. 170°–171° C. (dec.).
Analysis: $C_{17}H_{21}N_5O_5S$: Found %: C-49.87; H-5.33; N-17.02. Calc. %: C-50.12; H-5.19; N-17.19.

(ak)

N-Isopropyl-N'-[2-methyl-4-(1,2,4-triazol-3-yl)-phenyl]-formamidine

Hydrochloride (acetone); M.p. 154°–156° C. (dec.).
Analysis: $C_{13}H_{19}Cl_2N_5$: Found %: C-49.19; H-6.17; N-22.04. Calc. %: C-49.37; H-6.05; N-22.15.

The compounds embraced by formula I above and their nontoxic, pharmacologically acceptable acid addition salts have useful pharmacodynamic properties. More particularly, they exhibit antiulcerogenic and gastric acid secretion inhibiting activities in warm-blooded animals such as rats.

The antagonistic activity of the compounds of the invention on histamine H$_2$-receptors is demonstrated either in vitro or in vivo by their inhibition of the H$_2$-dependent biological effects, which include the histamine-evoked positive chronotropic effect and the histamine-induced gastric secretion of acid respectively.

The inhibition of the positive chronotropic effect was investigated on isolated guinea pig atria suspended in an organ bath (50 ml) containing an oxygenated ($O_2$:95%-$CO_2$:5%) Krebs-Henseleit solution (pH 7.4) maintained at 32° C. The myocardial preparation, loaded with 1 g isometric tension, was allowed to stabilize 60 minutes, and myocardial contractions were recorded through an isometric lever connected to a strain-gauge coupler and the instantaneous rate was monitored with a cardiotachometer, and a heatwriting pen recorder. After two control responses to histamine ($10^{-6}$ g.ml$^{-1}$) the test compound was added to the bath at the desired final concentration and left for 30 minutes before the atria were again challenged with histamine. The chronotropic response obtained in the presence of the antagonist was then compared to the control response to histamine, and the percent reduction of the histamine $H_2$-evoked response was calculated. The average effective concentration ($EC_{50}$) of the $H_2$-antagonists was also calculated by standard procedure according to Dr. Waud, Analysis of Dose-Response Curves, in "Methods in Pharmacology" vol. 3, Smooth muscle, Ed. Daniel E. E. Paton, M., Plenum Press, New York (1975); Ash and Schild, Br. J. Pharmacol. Chemother. 27, 427–439, 1966. The following table shows the results which were obtained.

TABLE I

| In vitro inhibitory activity in histamine induced tachycardia (guinea pig atria). | |
|---|---|
| Compound of Example | $EC_{50}$ $10^{-7}$ M |
| 10 (a) | 3.90 |
| 10 | 9.95 |
| CIMETIDINE | 34.00 |

The ability of the test compounds to inhibit histamine-induced gastric secretion of acid was investigated after intravenous or intraduodenal administration in stomach-perfused rats, according to Gosh and Schild (Br. J. Pharmacol. Chemother. 13, 54, 1958).

The preparation of the animals under general anesthesia (urethane, 1 g.kg$^{-1}$ i.p.) and constant temperature, was achieved by inserting and tying in place polyethylene tubes (PE 50) in the esophagus and in the pyloric-antral region. After the stomach was washed to remove residual of foods, continuous perfusion of the stomach was started with saline, 0.5 ml.min$^{-1}$ (37° C.), primed by a Jobling peristaltic pump. After 30 minutes of perfusion adaptation, the stomach perfusate was collected in 30 minute samples, and titrated for acid content, expressed as $\mu$Eq of NaOH 1N. As control acid output became constant, intravenous perfusion of histamine (1 mg.kg$^{-1}$ hr$^{-1}$) was started and maintained throughout the experimental period. After the acid secretion had reached the steadily higher level, increasing doses of the test compound were injected intravenously in order to obtain dose-response functions. The $ED_{50}$ was then calculated by standard procedure.

The results are shown in the following table:

TABLE II

| In vivo antisecretory activity in histamine-induced gastric secretion (stomach-perfused rat). | |
|---|---|
| Compound of Example | $ED_{50}$ mg · kg$^{-1}$ (i.v.)* |
| 10 (a) | 0.185 |
| 10 | 0.121 |

TABLE II-continued

| In vivo antisecretory activity in histamine-induced gastric secretion (stomach-perfused rat). | |
|---|---|
| Compound of Example | $ED_{50}$ mg · kg$^{-1}$ (i.v.)* |
| CIMETIDINE | 0.560 |

*The values of activity are expressed taking the compound as a base.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, solutions, suspensions, emulsions, syrups, suppositories and the like. An effective amount of the compounds according to the present invention is from 0.14 to 7.14 mgm/kg body weight, preferably 0.28 to 2.14 mgm/kg body weight.

The following examples illustrate a few pharmaceutical compositions comprising a compound of the present invention as an active ingredient and represent the best modes contemplated of using the invention. The parts are parts by weight unless otherwise specified.

Example 11

Tablets

The tablet composition is compounded from the following ingredients:

| | |
|---|---|
| N—Isopropyl-N′—[4-(pyrazol-3-yl)-phenyl]-formamidine Hydrochloride | 50 parts |
| Lactose | 217 parts |
| Corn starch | 30 parts |
| Magnesium stearate | 3 parts |
| Total | 300 parts |

Preparation

The active ingredient, the lactose and the corn starch are mixed and homogeneously moistened with water. After screening of the moist mass and drying in a tray driver, the mixture is again passed through a screen and magnesium stearate is added. Then, the mixture is compressed into tablets weighing 300 mg each. Each tablet contains 50 mg of the active ingredient.

Example 12

Capsules

The capsule filler composition is compounded from the following ingredients:

| | |
|---|---|
| N—Isopropyl-N′—[4-(pyrazol-3-yl)-phenyl]-formamidine Hydrochloride | 50 parts |
| Corn starch | 170 parts |
| Magnesium stearate | 2 parts |
| Total | 222 parts |

Preparation

The active ingredient is mixed with the excipients, and the mixture is passed through a screen and homogeneously mixed in a suitable device. The resulting mixture is filled into hard gelatin capsules (222 mg per capsule); each capsule contains 50 mg of the active ingredient.

Example 13

Hypodermic solution

The solution is compounded from the following ingredients:

| | |
|---|---|
| N—Isopropyl-N'—[4-(pyrazol-3-yl)-phenyl]-formamidine Hydrochloride | 50 parts |
| Sterile water | 5000 parts by vol. |

Preparation

The active ingredient is dissolved in the water, and the resulting solution is filled into 5 cc-ampules under sterile conditions. Each ampule contains 50 mg of the active ingredient.

Any one of the other compounds embraced by formula I or a non-toxic, pharmacologically acceptable acid addition salt thereof may be substituted for the particular active ingredient in Examples 11 through 13. Likewise, the amount of active ingredient in these illustrative examples may be varied to achieve the dosage unit range set forth above, and the amounts and nature of the inert pharmaceutical carrier ingredients may be varied to meet particular requirements.

With the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

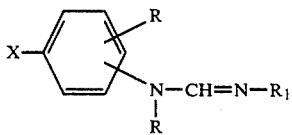

wherein
R is hydrogen or methyl;
$R_1$ is straight or branched alkyl of 1 to 6 carbon atoms, hydroxy(alkyl of 1 to 6 carbon atoms), mono- or di-(alkoxy of 1 to 6 carbon atoms) (alkyl of 1 to 6 carbon atoms), (alkyl of 1 to 6 carbon atoms)thio(alkyl of 1 to 6 carbon atoms), cyano(alkyl of 1 to 6 carbon atoms), alkenyl, alkynyl, or cycloalkyl;
$R_2$ is hydrogen, alkyl of 1 to 3 carbon atoms, alkoxy of 1 to 3 carbon atoms or halogen; and
X is pyrazol-3-yl, 1,2,4-triazol-3-yl, pyridin-2-yl, pyridin-3-yl, thiazol-4-yl, 2-methyl-thiazol-4-yl or 2-methylamino-thiazol-4-yl;
a tautomer thereof, or a non-toxic, pharmacologically acceptable acid addition salt thereof.

2. A compound of claim 1, where said acid addition salt is formed with maleic, hydrochloric, fumaric or sulfuric acid.

3. A compound of claim 1, wherein the formamidine radical is in the para-position on the benzene ring with respect to X.

4. A compound of claim 3, where
R is hydrogen,
$R_1$ is propyl, isopropyl, butyl, sec.butyl, isobutyl, neopentyl, allyl, methoxyethyl, dimethoxyethyl, hydroxypropyl, hydroxybutyl, methylthioethyl, ethylthioethyl or cyanoethyl;
$R_2$ is hydrogen, methyl, methoxy, bromine, chlorine or fluorine; and
X is pyrazolyl-3-yl or (1,2,4-triazolyl-3-yl);
a tautomer thereof, or a non-toxic, pharmacologically acceptable acid addition salt thereof.

5. A compound of claim 1, which is N-isopropyl-N'-[4-(pyrazol-3-yl)-phenyl]-formamidine or a non-toxic, pharmacologically acceptable acid addition salt thereof.

6. A compound of claim 1, which is N-isopropyl-N'-[4-(1,2,4-triazol-3-yl)-phenyl]-formamidine or a non-toxic, pharmacologically acceptable acid addition salt thereof.

7. An antiulcerogenic and gastric acid secretion inhibiting pharmaceutical composition consisting essentially of an inert pharmaceutical carrier and an effective antiulcerogenic and gastric acid secretion inhibiting amount of a compound of claim 1.

8. The method of treating gastric ulcers and inhibiting gastric acid secretion in a warm-blooded animal in need thereof, which comprises perorally or parenterally administering to said animal an effective antiulcerogenic and gastric acid secretion inhibiting amount of a compound of claim 1.

9. A compound of the formula

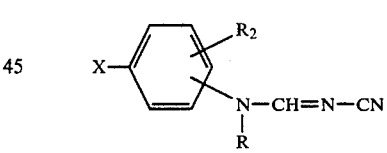

wherein
R is hydrogen or methyl;
$R_2$ is hydrogen, alkyl of 1 to 3 carbon atoms, alkoxy of 1 to 3 carbon atoms or halogen; and
X is pyrazol-3-yl, 1,2,4-triazol-3-yl, pyridin-2-yl, pyridin-3-yl, thiazol-4-yl, 2-methyl-thiazol-4-yl or 2-methylamino-thiazol-4-yl.

* * * * *

UNITED STATES PATENT AND TRADEMARK OFFICE
CERTIFICATE OF CORRECTION

PATENT NO. : 4,699,915

DATED : October 13, 1987

INVENTOR(S) : ENZO CEREDA ET AL.

It is certified that error appears in the above-identified patent and that said Letters Patent is hereby corrected as shown below:

Column 2, line 21 and line 22: "when $R_1$ . . . hydroxybutyl" should be deleted.

Column 5, line 23: "brmoacetyl" should read -- bromoacetyl --.

Column 9, line 54: "N$\alpha$" should read -- N'- --.

Column 10, line 17: "(Pyrazol" should read -- (pyrazol --.

Signed and Sealed this

Twelfth Day of April, 1988

Attest:

DONALD J. QUIGG

Attesting Officer

Commissioner of Patents and Trademarks